(12) United States Patent
van der Ent et al.

(10) Patent No.: US 7,762,137 B2
(45) Date of Patent: Jul. 27, 2010

(54) METHOD FOR CHECKING A WELD BETWEEN TWO METAL PIPELINES

(75) Inventors: Jan van der Ent, Bosschenhoofd (NL); Jacobus Johannes M. van Nisselrolj, Arnhem (NL); Edwin Theodorus van Kessel, Ridderkerk (NL)

(73) Assignee: Rontgen Technische Dienst B.V., NC Rotterdam (NL)

(*) Notice: Subject to any disclaimer, the term of this patent is extended or adjusted under 35 U.S.C. 154(b) by 798 days.

(21) Appl. No.: 10/578,492

(22) PCT Filed: Nov. 8, 2004

(86) PCT No.: PCT/NL2004/000784

§ 371 (c)(1),
(2), (4) Date: Feb. 14, 2007

(87) PCT Pub. No.: WO2005/045418

PCT Pub. Date: May 19, 2005

(65) Prior Publication Data

US 2007/0261495 A1    Nov. 15, 2007

(30) Foreign Application Priority Data

Nov. 6, 2003 (NL) .................................. 1024726

(51) Int. Cl.
*G01N 29/00* (2006.01)
(52) U.S. Cl. .............................. 73/627; 73/620; 73/622; 73/628; 73/641
(58) Field of Classification Search .................. 73/627, 73/620, 622, 524, 625, 628, 641
See application file for complete search history.

(56) References Cited

U.S. PATENT DOCUMENTS 4,375,165 A    3/1983    de Sterke ..................... 72/622

(Continued)

FOREIGN PATENT DOCUMENTS

WO    WO01/71338    9/2001

OTHER PUBLICATIONS de Raad et al, Materials Evaluation, Aug. 1997, pp. 890-895, XP009006892, Mechanized Ultrasonic Testing on Girth Welds . . . .

*Primary Examiner*—J M Saint Surin
(74) *Attorney, Agent, or Firm*—Jacobson Holman PLLC (57) ABSTRACT

A method for checking a weld (1) between a first metal pipeline (2) and a second metal pipeline (4), in particular an austenitic weld, the method comprising at least the following method steps: (a) a first ultrasonic beam (30) is transmitted to an interface (26) between the weld and the first pipeline situated on a first side (28) of the weld; (b) a reflection of the first ultrasonic beam (30) on the interface (26) situated on the first side (28) of the weld is received and a first received signal corresponding thereto is generated; (c) a second ultrasonic beam (40) different from the first ultrasonic beam (30) is transmitted to the interface (26) situated on the first side (28) of the weld; (d) a reflection of the second ultrasonic beam (40) on the interface (26) situated on the first side (28) of the weld is received and a second received signal corresponding thereto is generated; (e) the first received signal and the second received signal are processed in combination for checking the weld (1).

47 Claims, 5 Drawing Sheets

U.S. PATENT DOCUMENTS

| | | | | |
|---|---|---|---|---|
| 4,516,429 A | * | 5/1985 | Haacke et al. | 73/638 |
| 4,541,064 A | * | 9/1985 | Livingston | 702/36 |
| 4,627,289 A | * | 12/1986 | Fukuda et al. | 73/622 |
| 4,709,582 A | * | 12/1987 | Besanceney | 73/622 |
| 5,392,652 A | * | 2/1995 | Levesque et al. | 73/629 |
| 5,677,490 A | * | 10/1997 | Gunther et al. | 73/622 |
| 6,332,361 B1 | * | 12/2001 | Yamada et al. | 73/627 |
| 7,168,322 B2 | * | 1/2007 | Bardoux et al. | 73/588 |
| 7,516,022 B2 | * | 4/2009 | Lee et al. | 702/39 |

* cited by examiner

METHOD FOR CHECKING A WELD BETWEEN TWO METAL PIPELINES

This is a nationalization of PCT/NL2004/000784 filed 8 Nov. 2004 and published in English.

The present invention relates to a method for checking a weld between a first metal pipeline and a second metal pipeline. In the Non-Destructive Testing (NDT) of circumferential welds during the construction of pipelines, increasingly stringent requirements are imposed on the reliability and the accuracy of the NDT method used. This is especially due to the wish to be able to trace ever smaller defects, specifically in offshore lines such as risers, which form the connection between offshore-platforms or FPSO's (Floating Production, Storage and Offloading vessels) and facilities on the seabed. These lines are fatigue-loaded, so that a small welding flaw may already form a crack initiation which can lead to serious accidents (for instance the loss of a platform and human lives) and ecological damage. Partly for that reason, in the regulations, the acceptability criteria for welding defects are more and more linked to fracture mechanics calculations, so that the requirements imposed on the NDT method regarding its capability of measuring the magnitude of defects once they have been detected, are becoming increasingly stringent as well.

In order to improve the quality of the welds, two metal pipelines are connected with each other in particular through an austenitic weld. A disadvantage of such a weld is that it is coarse-grained and anisotropic, so that the weld does not easily lend itself to ultrasonic testing.

The object of the invention is to provide a method whereby the checking of a weld between two metal pipelines, in particular an austenitic weld, can be improved as regards reliability and whereby moreover the magnitude of a detected defect can be determined, if such is desired.

The method for checking a weld is accordingly characterized in that the method comprises at least the following method steps:

a. a first ultrasonic beam is transmitted to an interface between the weld and the first pipeline situated on a first side of the weld;
b. a reflection of the first ultrasonic beam on the interface situated on the first side of the weld is received and a first received signal corresponding thereto is generated;
c. a second ultrasonic beam different from the first ultrasonic beam is transmitted to the interface situated on the first side of the weld;
d. a reflection of the second ultrasonic beam on the interface situated on the first side of the weld is received and a second received signal corresponding thereto is generated;
e. the first received signal and the second received signal are processed in combination for checking the weld.

Owing to the use of two mutually different ultrasonic beams, more information on the weld to be checked is obtained than with one ultrasonic beam, so that the reliability of the check of the weld can be improved.

In particular, it holds that the first and the second ultrasonic beam at the interface between the weld and the first pipeline have a mutually different angle of incidence on the interface.

More particularly, it holds that in step a. the first ultrasonic beam is directed such that the direction in which the first ultrasonic beam is incident on the interface between the weld and the first pipeline deviates from the normal to a surface of the interface between the weld and the first pipeline at the point where the first ultrasonic beam is incident on the interface. What holds here, preferably, is that in step a. the first ultrasonic beam is supplied to the interface between the weld and the first pipeline via the first pipeline. Further, it holds here, in particular, that in step b. the reflection of the first ultrasonic beam is measured that comes from a direction that deviates from the direction in which the first ultrasonic beam would reflect on the interface according to the rule that the angle of incidence is equal to the angle of reflection, so that the first ultrasonic received signal represents a diffraction, if any, of the first ultrasonic beam on a flaw in the weld at the interface between the weld and the first pipeline. All this means that in step b. the first ultrasonic received signal comprises information of a possible flaw on the interface between the weld and the first pipeline because especially the ends of any flaw will cause diffraction of the first ultrasonic beam. Because the first beam is directed such that the direction of the first beam at the interface between the weld and the first pipeline deviates from the normal to a surface of the interface between the weld and the first pipeline, the first received signal will contain relatively little information (small amplitudes) of a reflection of the first ultrasonic beam on the interface between the weld and the first pipeline resulting from a transition between the medium of the first pipeline and the medium of the weld. Consequently, the diffraction, if any, resulting from a flaw can be determined relatively well.

In particular, it holds that in step a. the first ultrasonic beam is supplied to the interface between the weld and the first pipeline via the first pipeline. Further, it holds in particular that in step a., for the first ultrasonic beam a longitudinal wave is used. If for the first ultrasonic beam a longitudinal wave is used, this provides the advantage that diffraction can be measured relatively well. If a transverse wave were used, enormous reflections would be measured, making it more difficult to determine the diffraction, if any, resulting from a flaw.

Preferably, it holds further that in step c. the second beam is directed such that the direction in which the second beam is incident on the interface between the weld and the first pipeline, at least substantially does not deviate from the normal to a surface of the interface between the weld and the first pipeline. Then it furthermore holds, preferably, that in step d. a reflection of the second ultrasonic beam is measured that comes from a direction which, at least substantially, coincides with the direction in which the second ultrasonic beam is incident on the interface between the weld and the first pipeline. The result is that the second received signal comprises relatively much (large amplitudes) information on any flaw of the weld at the interface between the weld and the first pipeline. The second received signal will then specifically include information of reflections of any flaw of the weld between the weld and the first pipeline. Such reflections are generally stronger than reflections resulting from a transition between the medium of the weld and the medium of the first pipeline.

In particular, it holds that in step c. the second ultrasonic beam, after being transmitted, first of all propagates through the second pipeline to an interface between the second pipeline and a second side of the weld, situated opposite the first side of the weld, after which the second ultrasonic beam proceeds to propagate through the weld to the interface between the weld and the first pipeline. It furthermore holds here, in particular, that in step c. for the second ultrasonic beam a longitudinal wave is used. Because the second ultrasonic wave, as discussed above, is to propagate in particular through the weld proper, preferably a longitudinal wave is used because if the weld is of austenitic material, it is precisely a longitudinal wave that can propagate through it relatively well. An austenitic weld has a granular structure which forms an anisotropic material. If for the second ultrasonic beam a transverse wave were used, there would be relatively many reflections within the anisotropic material, so that the strength of the second received signal will decrease dramatically, rendering it very difficult to find any information in the second received signal on any flaw in the weld.

If it presently appears that both the first received signal and the second received signal indicate that a flaw may be present, it may be concluded that the weld indeed comprises a defect at the respective interface. In other words, it holds that in step e. it is determined on the basis of the first received signal whether the weld may comprise a defect and it is determined on the basis of the second received signal whether the weld may comprise a defect, it being concluded that the weld actually comprises a defect when both on the basis of the first received signal and on the basis of the second received signal it is concluded that the weld may comprise a defect.

According to a highly advanced embodiment of the method, it holds that the method furthermore comprises at least the following method steps:

f. a third ultrasonic beam is transmitted to the interface between the weld and the first pipeline situated on the first side of the weld;

g. a reflection of the third ultrasonic beam on the interface situated on the first side of the weld, according to the rule that the angle of incidence is equal to the angle of reflection on the surface of the interface between the weld and the first pipeline is received and a third received signal corresponding thereto is generated; and h. the third received signal is analyzed for checking the weld.

In particular, it holds here that the third beam is directed such that the direction in which the third beam is incident on the interface between the weld and the first pipeline generally deviates from the normal to a surface of the interface between the weld and the first pipeline at the point where the third beam is incident on the interface between the weld and the first pipeline. Further, it holds here, in particular, that in step g. the reflection of the third ultrasonic beam is measured that comes from a direction which, at least substantially, coincides with the direction in which the third ultrasonic beam would reflect on the interface according to the rule that the angle of incidence is equal to the angle of reflection, so that the third ultrasonic received signal represents any reflection of the third ultrasonic beam on a possible flaw at the interface between the weld and the first pipeline. More particularly, it holds here that in step g. on the basis of an amplitude of the third received signal, the magnitude of any defect is determined.

Preferably, it holds that in step f. the third ultrasonic beam is supplied to the interface between the weld and the first pipeline via the first pipeline. Further, it preferably holds that in step f., for the third ultrasonic beam a transverse wave is used. This brings with it that, precisely because a transverse wave is used, a flaw, if any, at the interface between the weld and the first pipeline will cause well-measurable reflections. The magnitude of the reflection can then correspond to the magnitude of the measured flaw.

According to a highly advanced embodiment, it holds that on the basis of the third received signal, the magnitude of the defect is determined if on the basis of the performance of the method step e. it appears that the weld comprises a defect. This brings with it, in particular, that when on the basis of the first and second received signal it is concluded that the weld comprises a defect, the magnitude of the defect is subsequently determined on the basis of the third received signal.

According to a highly efficient embodiment of the method according to the invention, it holds that an interface between the weld and the second pipeline is checked as the interface between the first pipeline and the weld is checked, while the first ultrasonic beam is also used for checking the interface between the second pipeline and the weld in a same way as the second ultrasonic beam is used for checking the interface between the weld and the first pipeline.

All this means that the first ultrasonic beam can be used for checking both the interface of the weld between the first pipeline and the weld, and the interface of the weld between the second pipeline and the weld. Likewise, it holds, preferably, that an interface between the weld and the second pipeline is checked as the interface between the first pipeline and the weld is checked, while the second ultrasonic beam is also used for checking the interface between the second pipeline and the weld in a same way as the first ultrasonic beam is used for checking the interface between the weld and the first pipeline. In that case, the second ultrasonic beam can be used for checking the interface of the weld on the side of the first pipeline as well as the interface of the weld on the side of the second pipeline.

Each interface of the weld can be examined according to the method as described above using the first, second and third beams. The interface is then divided up into small areas and each area is irradiated with the first and second ultrasonic beams. If there proves to be a flaw, additionally the magnitude of the flaw in such an area can be determined with the third ultrasonic beam.

The invention will presently be further elucidated with reference to the drawing. In the drawing:

FIG. 1b shows a cross section of the complete weld and pipelines of FIG. 1a;

Figure 1A:
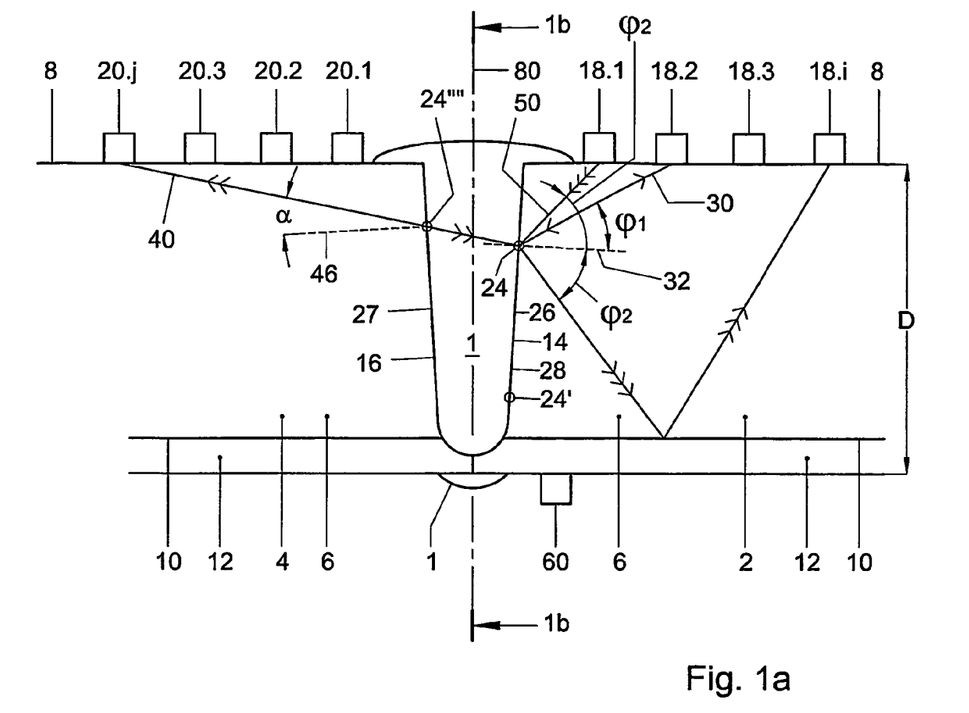
FIG. 1a shows a cross section of a part of two pipelines which are connected with each other through an austenitic weld, as well as a part of an apparatus for carrying out a method according to the invention.
Figure 1B:
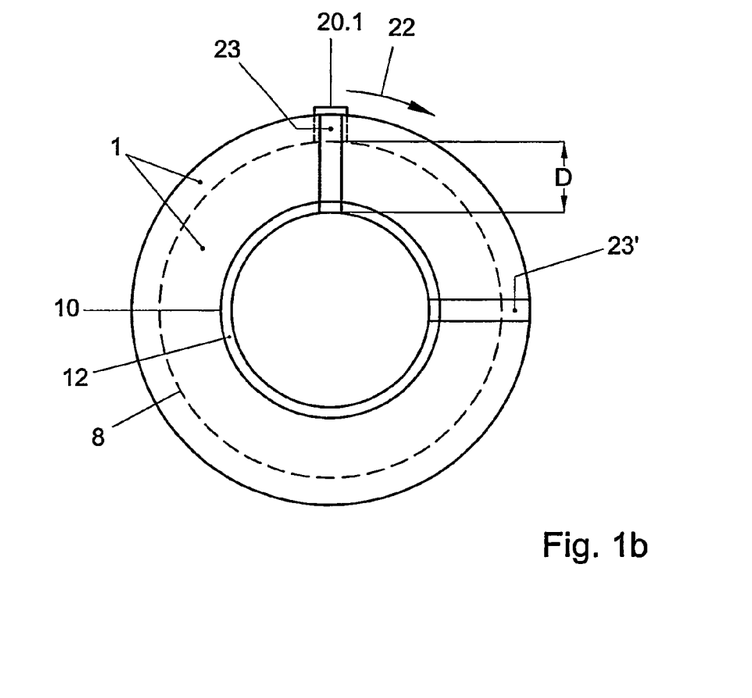

In FIG. 1a, reference numeral 1 designates a weld between a first metal pipeline 2 and a second metal pipeline 4. FIG. 1 shows a cross section of a wall 6 of the pipelines. Each pipeline 2, 4 is provided with an outer wall 8 and an inner wall 10, the inner wall 10 in this example being provided with a cladding layer 12.

In this example, the wall of the first and the second pipeline therefore has a thickness D as is indicated in FIG. 1. In FIG. 1b, here is shown a cross section of the weld and pipelines.

The shape of the first end 14 of the first pipeline 2 as well as the shape of the second end 16 of the second pipeline 4 is fixed. Thus, at the same time, basically the shape of the weld 1 is fixed. In this example, the pipelines are each made of carbon steel. The weld 1 is an austenitic weld.

For carrying out the method according to the invention, use is made of a plurality of ultrasonic probes 18.*i*, known per se, which abut against the outer wall 8 of the first pipeline 2. Furthermore, use is made of a plurality of ultrasonic probes 20.*j* which abut against the outer side 8 of the second pipeline 4. In use, the probes will be moved in a tangential direction 22 (see FIG. 1*b*) around the pipelines 2 and 4, allowing the whole circumferential weld 1 to be examined. In this example, it is indicated how a segment 23 of an interface 26 between the weld 1 and the first pipeline 2 on a first side 28 of the weld can be examined for checking the weld 1. For checking other segments 23', the probes are moved in the tangential direction 22. More particularly, it will first of all be discussed how a small area 24 which is situated at a particular point of the interface between the first pipeline 2 and the weld 1 in the segment 23 can be tested. Other areas 24' are situated in radial direction 25 relative to the area 24.

For checking the area 24, in this example, using the probe 18.2, a first ultrasonic beam 30 is transmitted to the area 24. This method step will hereinafter be designated as method step a. Next, in a method step b., a reflection of the first ultrasonic beam on the interface situated on the first side 28 of the weld is received, and a first received signal corresponding thereto is generated. In this example, it holds that in step a. the first beam 30 is directed such that the direction in which the first beam is incident on the interface between the weld and the first pipeline deviates from the normal 32 to a surface of the interface between the weld and the first pipeline at the point where the first beam is incident on the interface. In this example, this is the normal 32 to the surface of the area 24 of the interface 26. It includes an angle $\phi 1$ with the incident first beam 30. Furthermore, it holds, as is apparent from the drawing, that in this example the first ultrasonic beam is supplied to the interface 26 via the first pipeline 2. It also holds that the first ultrasonic beam is supplied to the first pipeline from an outer side of the first pipeline. For the first ultrasonic beam, a longitudinal wave is used. Furthermore, it holds that the first ultrasonic beam is a pulsed wave. It holds in this example, furthermore, that in step b. the reflection of the first ultrasonic beam is measured that comes from a direction that deviates from the direction in which the first ultrasonic beam would reflect on the interface according to the rule that the angle of incidence is equal to the angle of reflection, so that the first ultrasonic received signal represents a diffraction, if any, of the first ultrasonic beam on the interface between the weld and the first pipeline. More preferably, it holds that in step b. the reflection of the first ultrasonic beam is measured that comes from a direction which, at least substantially, coincides with the direction in which the first ultrasonic beam is incident on the interface between the first pipeline and the weld.

In this example, it holds furthermore that the reflection of the first ultrasonic beam 30 that is measured, is received with the same ultrasonic probe as that with which the first ultrasonic beam has been transmitted.

Figure 1C:
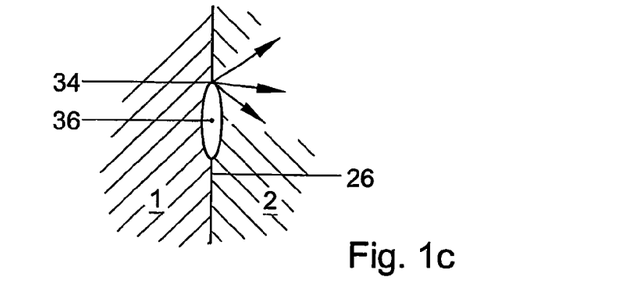
FIG. 1c shows an example of a possible flaw between the weld and the first pipeline.

If in the area 24 a flaw is present, for instance in that in the area 24 the weld 1 is not connected with the first end 14 of the first pipeline or in that small air bubbles are included at that point, this will have as a consequence that diffraction of the first ultrasonic beam on the flaw occurs. This diffraction occurs especially at an end of a flaw 36, in this example a missing connection between the weld 1 and the pipeline 2 as shown in FIG. 1*c*. Diffraction entails the first ultrasonic beam being reflected in more than one direction. Besides diffraction, the first beam will also for a part be reflected on the flaw. Moreover, a portion of the first beam will be reflected as a result of the transition between the medium of the first pipeline (carbon steel) and the weld (austenitic material).

Figure 1D:
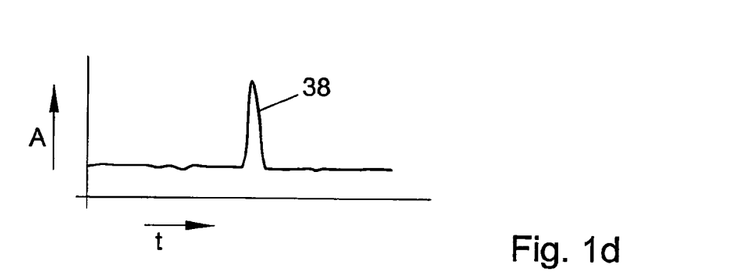
FIG. 1d shows an example of a first received signal.

Because in this example in step b. the reflection of the first ultrasonic beam is measured that comes from a direction that deviates from the direction in which the first ultrasonic beam would reflect on the interface according to the rule that the angle of incidence is equal to the angle of reflection, so that the first ultrasonic received signal represents a diffraction, if any, of the first ultrasonic beam on the interface between the weld and the first pipeline, relatively few reflections of the first beam on the flaw and/or the interface proper will be measured with the ultrasonic probe 18.2, and specifically a diffraction, if any, on the flaw will be measured. Such a diffraction is characterized in a peak 38 in the amplitude A of the first received signal as shown in FIG. 1*d*. Such a peak 38 is a good indication that a flaw at the interface 26 of the weld is present in the area 24. For transmitting the first ultrasonic beam, preferably a longitudinal wave is used because a transverse wave will generate unwanted reflections which make it difficult to measure the diffractions.

The method according to the invention furthermore comprises the following method steps:

in a method step c., a second ultrasonic beam 40, different from the first ultrasonic beam 30, is transmitted to the interface situated on the first side of the weld. In this example, it holds that the first and the second ultrasonic beams at the interface between the weld and the first pipeline have a mutually different angle of incidence on the interface. More particularly, it holds that in step c. the beam 40 is directed such that the direction in which the second beam is incident on the interface between the weld and the first pipeline at least substantially does not deviate from the normal 32 at the point where the second beam 40 is incident on the interface. For this purpose, in this example, the second ultrasonic beam is supplied to the interface between the weld and the first pipeline via the second pipeline and the weld, using the ultrasonic probe 20.*j*. The second ultrasonic beam, after being transmitted by the ultrasonic probe 20.*j*, will first of all propagate through the second pipeline 4 to the interface 27 between the second pipeline 4 and the weld 1, after which the ultrasonic beam proceeds to propagate through the weld to the interface 26 between the weld and the first pipeline. In this example, the second ultrasonic beam is again a pulsed wave. Furthermore, the second ultrasonic beam is a longitudinal wave, which moreover is focused. Owing to a longitudinal wave being used, it can propagate relatively well through the austenitic material. If a transverse wave were used, this wave would be scattered in many directions owing to the granular structure of the austenitic material, which structure is anisotropic.

In step d. a reflection of the second ultrasonic beam is measured that comes from a direction at least substantially coinciding with the direction in which the second ultrasonic beam would reflect on a surface of the interface at the point where the second beam is incident on the interface.

In this example, it holds moreover that in step d. a reflection of the second ultrasonic beam is measured that comes from a direction which, at least substantially, coincides with the direction in which the second ultrasonic beam is incident on the interface between the weld and the first pipeline. All of this means that in this example the second ultrasonic beam is transmitted and received with one and the same probe.

Figure 1E:
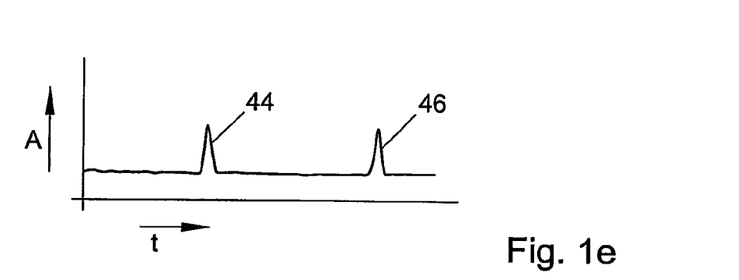
FIG. 1e shows an example of a second received signal.
Figure 1F:
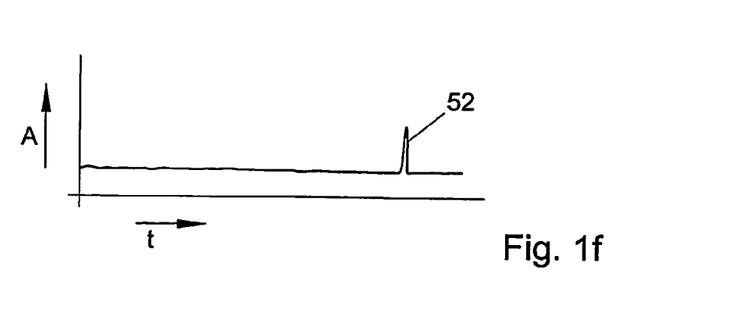
FIG. 1f shows an example of a third received signal.

Owing to the second ultrasonic beam being directed at least substantially perpendicularly to the interface, in this example the area 24 thereof, any flaw 36 will properly reflect the second ultrasonic beam. Since moreover a reflection is measured in a direction which corresponds to the expected direction of the reflected second beam, this reflection, if any, is measured well. All this is shown in FIG. 1e. The second received signal as shown in FIG. 1e shows first of all a peak 44 which is caused by a reflection of the second ultrasonic beam 40 on the second interface 27 between the weld 1 and the second pipeline 4. Since as a result of the shape of the weld the direction of the incident second ultrasonic beam deviates from the normal 46 to the interface 27 at the point where the second beam is incident on the second interface 27 (see angle α), the thus received reflection on the second interface will be relatively small. Owing to the second ultrasonic beam being incident at least substantially perpendicularly on the interface at the area 24, while a reflection of the second beam is measured in a direction corresponding to the expected reflection direction of the second beam, any flaw 36 in the area 24 of the interface 26 will generate a relatively large reflection. This reflection results in a well-measurable peak 46 in the received signal. Both for FIG. 1d and for FIG. 1e, it holds that the time at which a peak 38, 46 is received is a measure for a position in the material where the diffraction (FIG. 1d) and the reflection (FIG. 1e) have taken place. If presently it is determined both on the basis of the first received signal and on the basis of the second received signal that a flaw may be present in the area 24, it is decided that a flaw is actually present. To that end, the first and second received signals are, for instance as discussed above, detected separately from each other. This means that a received diffraction from the area 24 of the first beam can be distinguished from a received reflection from the area 24 of the second beam. More particularly, this can be carried out as follows. The amplitude of the first received signal can be compared with a first reference to determine whether the weld at the area 24 may comprise a flaw. Furthermore, the amplitude of the second received signal can be compared with a second reference to determine whether the weld at the area 24 may comprise a defect. The first and the second references may for instance have been pre-determined on the basis of a weld which in effect comprises a flaw at the area 24, or on the basis of reflections and measuring objects which can simulate such a flaw. It is concluded that the weld actually comprises a flaw when both on the basis of the first received signal and on the basis of the second received signal it is concluded that the weld may comprise a defect. hi this example, it holds that the first ultrasonic beam and the second ultrasonic beam are incident at least substantially on a same area of the interface between the first pipeline and the weld in order for this area of the interface to be checked.

Because in this example the beam width of the first and second beam (at least the beam width of the main beams of the first and second beam) does not cover the entire interface, the position of the area 24 (or any area 24 being checked) is thus known as well. The main beams mentioned each cover (in particular substantially) the area 24.

In particular, it holds that the first ultrasonic beam and the second ultrasonic beam are directed to a same area of the interface between the first pipeline and the weld.

Once it has been determined whether the weld at the area 24 comprises a flaw, it can optionally be examined with a third ultrasonic beam 50 what the magnitude of the flaw is. To that end, in a method step f., the third ultrasonic beam 50 is transmitted to the first side of the weld between the weld and the first pipeline, viz. to the area 24. It therefore holds that the third ultrasonic beam is incident at least substantially on the same area referred to. Here too, it holds that a beam width of the third ultrasonic beam (at least of the main beam) does not cover the entire interface. This main beam covers in particular at least substantially the area 24. In the example discussed, it holds that the third ultrasonic beam is directed to such area of the interface between the first pipeline and the weld.

The idea is that the magnitude of the reflection on a flaw in the weld is a measure of the magnitude of the flaw in the area 24. As shown in FIG. 1a, the third ultrasonic beam 50 that is transmitted by means of the probe 18.1 will reflect due to the flaw 36 in the weld in the direction of the inner side 10 of the pipeline. Thereupon, the third ultrasonic beam will reflect according to the rule of the angle of incidence being equal to the angle of reflection, on the inner wall of the pipeline, after which the reflected beam can be received by the probe 18.1. The assumption here is that the inner side of the pipeline is such that it can properly reflect the third ultrasonic beam. Preferably, it holds that the third ultrasonic beam is a transverse wave because it is precisely transverse waves that can properly reflect according to the law of the angle of incidence being equal to the angle of reflection with smooth surfaces. The defect 36 will generally extend in the direction of the interface 26, so that a reflection of the third ultrasonic beam 30 will take place in a direction that satisfies the law of the angle of incidence being equal to the angle of reflection relative to the direction of the plane of the interface at the area 24. If the defect 36 were not present, what results then is solely a reflection in this direction as a result of the transition of the medium of the first pipeline and the weld. However, this reflection is much smaller than a reflection of any flaw in the weld, so that in the latter case the magnitude of the reflection is, at least substantially, determined by the magnitude of the flaw in the weld. Precisely because transverse waves are used, this defect is properly measurable because transverse waves can properly reflect according to the rule of the angle of incidence being equal to the angle of reflection at any fault in the weld. Accordingly, it preferably holds that in step g. the reflection of the third ultrasonic beam is measured that comes from a direction at least substantially coinciding with the direction in which the third ultrasonic beam would reflect on the interface according to the rule that the angle of incidence is equal to the angle of reflection, so that the third ultrasonic received signal represents a reflection, if any, of the third ultrasonic beam on a possible flaw at the interface between the weld and the first pipeline.

With the ultrasonic probe 18.i, next, a third received signal is generated. Here too, it holds that the third ultrasonic wave is a pulsed wave. If the transmitted pulse is received and causes a peak 52 in the third received signal, the magnitude of the flaw can be assessed on the basis of the magnitude of the peak 52. The reflection on the interface resulting from the transition of the medium of the first pipeline to the medium of the weld is generally much less strong than the reflection resulting from a flaw (air between weld and first pipeline) at the interface. That the peak 52 is indeed a result of the reflection on the area 24 can be checked on the basis of the time at which the peak 52 is received. For if the time at which the pulse is transmitted by the probe 18.2 is known and if the position of the probes 18.2 and the probes 18.i relative to the segment 24 is known, while moreover the thickness D of the first pipeline is known, it can be calculated how much time the transmitted pulse requires to reach the probe 18.i via reflection on the area 24 and reflection on the inner side 10 of the first pipeline. The magnitude of the possible defect can be determined by comparing the amplitude with a reference, all this entirely analogously to what has been discussed above. The reference in turn can have been determined on the basis of the amplitude that has been measured on a reference object. Determining the magnitude of the defect of a weld can be carried out in particular when in method step e. it appears that the weld comprises a defect. If this proves to be the case, the magnitude of the defect can then be determined. Next, entirely analogously, by means of a first beam and a second beam, another area 24' can be examined to assess whether a flaw may be present there. The first and second beams are then directed towards this area 24'. This can be effected by moving the probes or using other probes.

Additionally, if it appears that a flaw is present in the area 24', it can then be determined what the magnitude of the flaw in the area 24' is in a manner entirely analogously to that described for the area 24, using a third ultrasonic beam which covers the area 24'. For this purpose too, the probes can be moved or other probes can be used for directing the third ultrasonic beam. Each interface of the weld can be tested according to the method as described above, using the first, second and third beams. The interface is then divided up into areas and each area is irradiated with the first and second ultrasonic beams. If there appears to be a flaw, further, by means of the third ultrasonic beam, the magnitude of the flaw in such an area can be determined.

Figure 2:
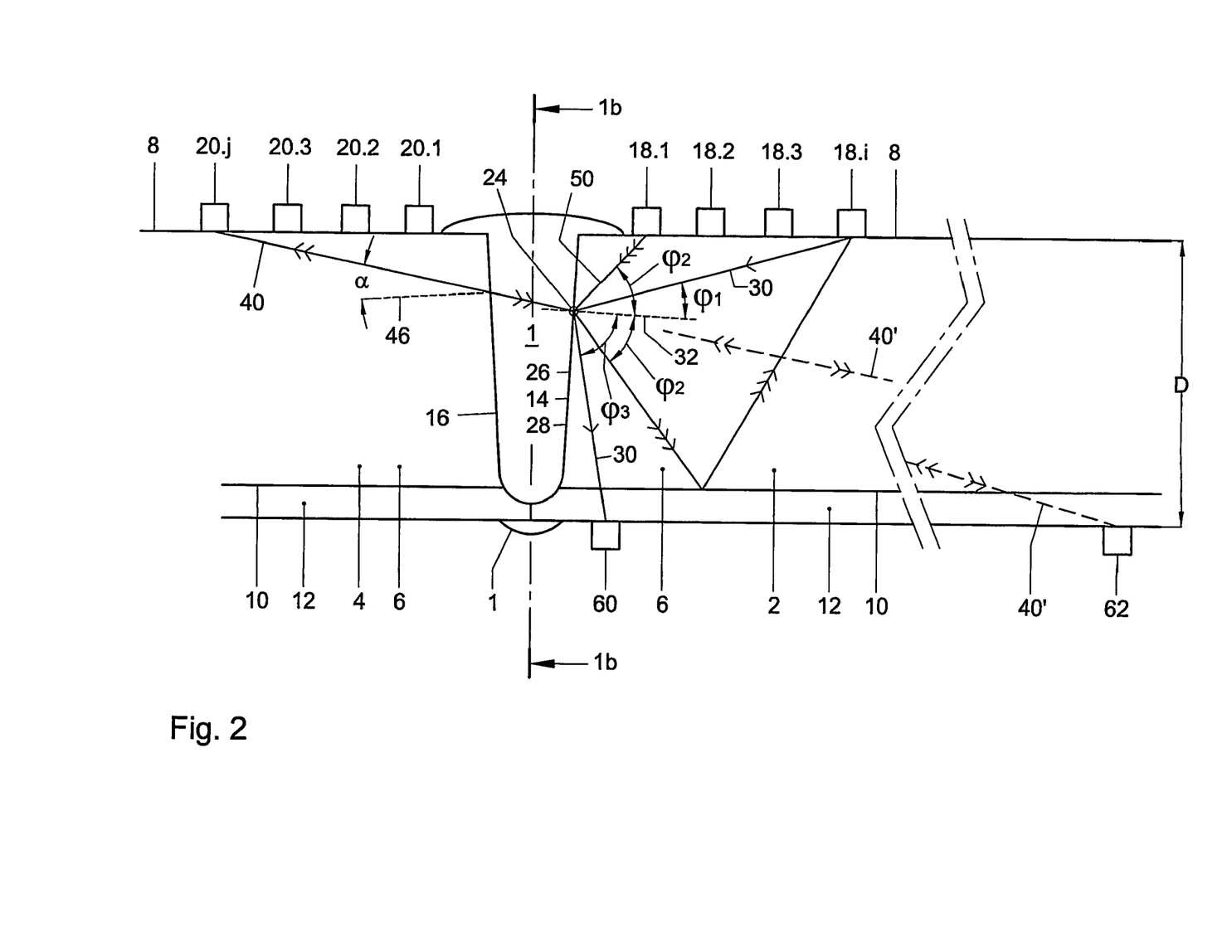
FIG. 2 shows a cross section of a part of two portions of pipelines which are connected with each other through an austenitic weld and a part of an apparatus for carrying out a first alternative embodiment of a method according to the invention.

The invention is not limited in any way to the embodiments outlined above. As stated, it holds in step b. that the reflection of the first ultrasonic beam is measured that comes from a direction that deviates from the direction in which the ultrasonic beam would reflect on the interface according to the rule that the angle of incidence is equal to the angle of reflection. What is thus accomplished is that precisely any diffractions of the first ultrasonic beam resulting from flaws at the interface between the weld and the first pipeline are measured. Any reflections resulting from such a flaw and/or reflections resulting from the medium transition from the pipeline to the weld, will be measured rather in other directions. If it is preferred that the ultrasonic probes are situated on the outer side of the pipeline, increasing the φ1 in FIG. 1*a* will have as a result that the discriminatory power between measurements of diffractions on the one hand and reflections on the other increases. If specifically no reflections are to be measured, it is moreover preferred to use the same probe for receiving the first ultrasonic beam as the one used for transmitting it. For in that case, too, it is precisely any diffraction that is measured, and not any reflection. It is also possible, however, for a diffraction of a the first ultrasonic beam to be received with, for instance, a different probe, such as probe 18.3. It is also possible that any diffraction is measured with a probe 60 situated on an inner side of the pipeline. The first ultrasonic beam (see FIG. 2) can then be transmitted, for instance, by means of the probe 18.*i* and be received after reflection by the probe 60. Because the angle φ1 deviates from the angle φ2, again especially any diffractions on flaws will be measured, and no reflections. It is, of course, possible here that the first ultrasonic beam is transmitted with the probe 60, to be subsequently received with the probe 18.*i*.

Figure 3:
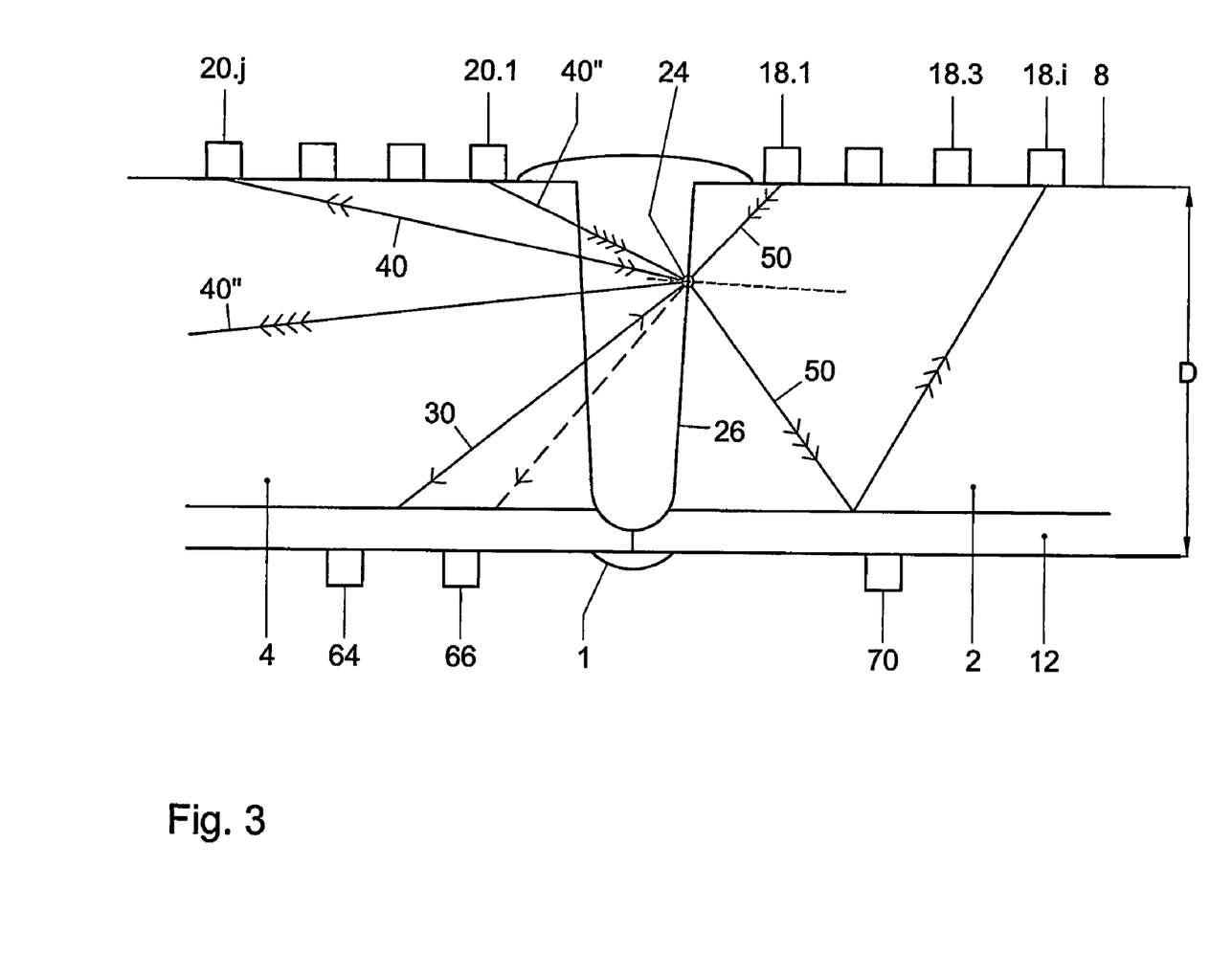
FIG. 3 shows a cross section of a part of two portions of pipelines which are connected with each other through an austenitic weld and a part of an apparatus for carrying out a second alternative embodiment of a method according to the invention.

In this example, it holds that in step c., the second beam, conversely, is intended to measure reflections resulting from any flaw. These reflections have been found to be maximal precisely when the second beam is at least substantially perpendicularly incident on the interface. Practically, the probes 20 can be arranged most easily on an outer side of the pipeline. Because the thickness of the weld increases in a direction from the inner side 10 of the wall 6 towards the outer side 8 of the wall, it is preferred in this example to supply the second ultrasonic beam to the second pipeline, after which it propagates via the second pipeline through the weld to the first interface 26. Theoretically, however, it is possible to transmit a second ultrasonic beam 40' with a probe 62 that is situated on an inner side of the pipeline. In this way, too, the interface 26 can be irradiated, at least substantially, perpendicularly. However, a drawback is that the distance between the probe 62 and the interface 26 is relatively large and that the probe 62 must be situated on an inner side of the first pipeline (see also FIG. 2). Because the second ultrasonic beam 40' does not need to propagate through the austenitic welding material, it is possible, instead of a longitudinal wave, to use a transverse wave for the second beam 40'. The use of transverse waves then actually provides the advantage that strong reflections are obtained. The second ultrasonic beam could also be transmitted, as shown in FIG. 3, with a probe 20.1 instead of the probe 20.*j*. This second ultrasonic beam is indicated by reference numeral 40". A reflection according to the rule that the angle of incidence is equal to the angle of reflection on any flaw of the weld at the area 24 can be measured by means of a probe (not shown in FIG. 3) which is situated on the inner side of the second pipeline. Here too, this entails the disadvantage that at least one probe must be placed on the inner side of the second pipeline and that moreover, as appears clearly from FIG. 3, in view of the shape of the weld, the path length which the second ultrasonic beam 40" must travel after reflection is rendered relatively large, so that a flaw, if any, can be detected less accurately. Furthermore, it should be noted that the direction of the second ultrasonic beam 40" in FIG. 3 can also be reversed. In that case, the second ultrasonic beam is supplied on an inner side of the second pipeline and subsequently received by the ultrasonic probe 20.1.

It is also possible, as appears from FIG. 3, that the third ultrasonic beam 50 after reflection on the interface is received by means of a probe 70 which is situated on the inner side of the first pipeline. This is advantageous in particular when the cladding 12 is a so-called welded cladding which does not properly reflect the third ultrasonic beam in the direction of the probe 18.*i*. If it is desired to use the probe 18.*i* anyway, what may be considered is the use of a longitudinal wave for the first beam, so that after the poor reflection on the cladding 12 still a reasonable signal is measured by the probe 18.*i*.

Also for transmitting the first ultrasonic wave, probes situated on an inner side of the first or second pipeline can be used. In the example of FIG. 3, a probe 64 is used which is situated on an inner side of the second pipeline, for transmitting and receiving the first ultrasonic wave 30. Because in this example the first ultrasonic wave is a longitudinal wave, it can also propagate well through the austenitic weld 1. Any diffractions of the first ultrasonic wave 30 could also be measured using, for instance, the probe 66 which is likewise situated on an inner side of the second pipeline. It is also conceivable that the diffractions referred to are measured by means of the probe 18.3 which is situated on an outer side of the first pipeline. Measuring diffractions using the probe 18.3 has as an advantage that the diffractions do not need to propagate back through the austenitic material of the weld to the second pipeline 4. What is needed instead is just propagation of the diffractions through the first pipeline 1, which in this example is fabricated from carbon steel, allowing good propagation of the sound waves. In both cases, it holds that the probes 64, 66 and 18.3 for the purpose of receiving diffractions of the first ultrasonic wave are set up such that no reflections of the ultrasonic wave on the interface 26 are measured.

Figure 4:
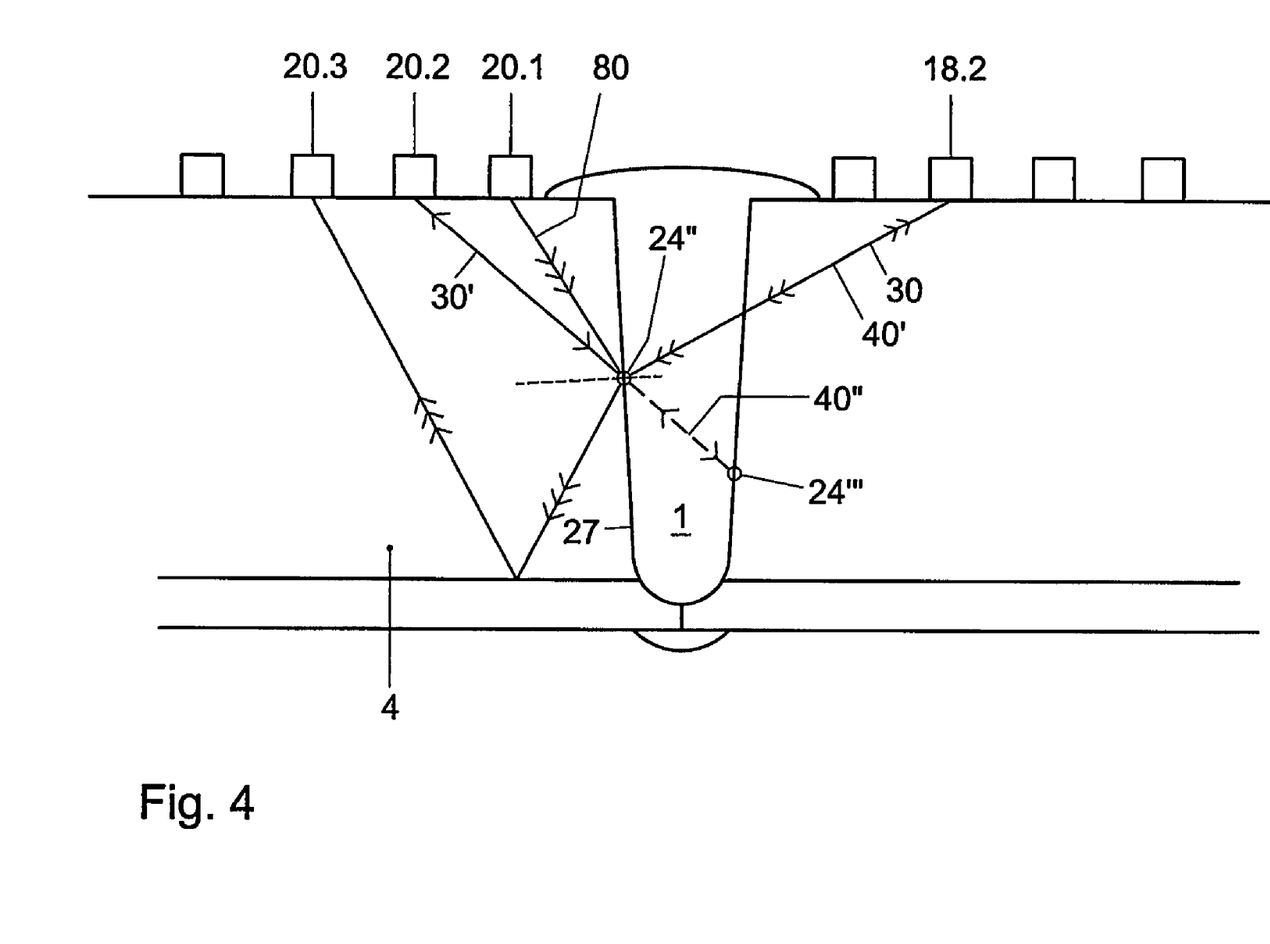
FIG. 4 shows a cross section of a part of two portions of pipelines which are connected with each other through an austenitic weld and a part of an apparatus for carrying out a third alternative embodiment of a method according to the invention.

As shown in FIG. 4, the first ultrasonic beam 30 which is transmitted in FIG. 1 by means of the probe 18.2 will also propagate to an area 24" of the interface 27 between the weld 1 and the second pipeline 4. A reflection of the first ultrasonic beam 30 on the interface 27 can also be measured by means of the probe 18.2. Then it holds here that for examining the area 24" of the interface 27 the first ultrasonic beam 30 can be used in a same manner as the second ultrasonic beam 40 has been used in FIG. 1. The first ultrasonic beam 30 accordingly functions in FIG. 4 as a second ultrasonic beam 40' for testing the interface 27. In FIG. 4, moreover, by means of the probe 20.2, a fourth ultrasonic beam 30' is transmitted to the area 24". The reflection of the beam 30' on the area 24" of the interface 27 is received by means of the ultrasonic probe 20.2, for generating a fourth received signal. The fourth beam has a same function at the area 24" as the first beam at the area 24. This fourth received signal can again comprise a peak resulting from diffraction of the fourth ultrasonic beam 30' on a flaw in the area 24". Entirely analogously to what has been discussed above, the first received signal can be combined with the fourth received signal. If both the first received signal and the fourth received signal indicate that a flaw may be present, it is concluded that a flaw is in fact present. Next, using the probe 20.1, a transverse beam 80 can be transmitted which after reflection on the interface and the inner side 10 of the second pipeline in the area proper 4, is received by means of the probe 20.3. The magnitude of the thus obtained received signal is used in this example for determining the magnitude of the flaw if it has been established on the basis of the first and fourth received signals that a flaw is actually present.

Accordingly, it holds that an interface between the weld and the second pipeline is checked as the interface between the first pipeline and the weld is checked, the first ultrasonic beam 30, 40' being also used for checking the interface between the second pipeline and the weld in a same manner as the second ultrasonic beam is used for checking the interface between the weld and the first pipeline. Also, it holds that in step b. also the reflection of the first ultrasonic beam on an interface of the weld between the weld and the second pipeline is measured to obtain the first received signal and that a fourth ultrasonic beam 30' is supplied to the interface of the weld between the weld and the second pipeline to obtain a fourth received signal, while the first and the fourth ultrasonic beams at the interface between the weld and the second pipeline have a mutually different angle of incidence on the interface between the weld and the second pipeline, and the first received signal and the fourth received signal are processed in combination for checking the interface between the weld and the second pipeline, in particular to determine whether the interface between the weld and the second pipeline comprises a defect. Here, the fourth ultrasonic beam and the fourth received signal correspond to the ultrasonic beam which is transmitted and received by means of the probe 20.2.

For the sake of completeness, it is noted that the fourth ultrasonic beam 30' again can function as a second ultrasonic beam 40" (see FIG. 4) for testing an area 24"' of the first interface 26. Moreover, it holds that an interface between the weld and the second pipeline can be checked as the interface between the first pipeline and the weld is checked, while the second ultrasonic beam 40 is also used for checking an area 24"' of the interface between the second pipeline and the weld in a same manner as the first ultrasonic beam is used for checking the interface between the weld and the first pipeline (see FIG. 1).

In the example of FIG. 1a, the area 24 has been examined. Entirely analogously, other areas of the interface 26 can be examined, with the first, second and third beams being analogously incident on the area 24'. It also holds, entirely analogously, that areas of the interface 27 can be examined, which is then done mirror-wise with respect to the plane 80 (see FIG. 1a).

The invention is not limited in any way to the embodiments outlined hereinbefore. More in general, additional information on a flaw can be found when the first and the second ultrasonic beams differ from each other. Preferably, it holds here that the first and the second ultrasonic beams between the weld and the first pipeline have a mutually different angle of incidence; more preferably, angles of incidence as discussed above are used.

Furthermore, in a step i., by means of the second ultrasonic beam, reflections can be measured in a fifth received signal, although this is not preferred, while in a step j., on the basis of the magnitude of the reflection on the interface as obtained by means of the second ultrasonic wave, the magnitude of the flaw is determined as well. Again, what holds is that the magnitude of the reflection (an amplitude in the fifth received signal) is a measure for the magnitude of the possible flaw of the weld at the interface 26. In this way, first of all, on the basis of the first received signal and the second received signal, it could be determined whether there is actually a flaw, whereupon on the basis of the magnitude of the above-mentioned peak in the second received signal an estimate of the magnitude of the flaw can be made. The frequency of the ultrasonic beams can for instance have the conventional values for this purpose in the art. Also, probes may be used which are capable of either sending or receiving. For the purpose of the first and second beam, a transmitting and a receiving probe will preferably be situated next to each other.

Also, a side beam of one of the ultrasonic beams, which, viewed in FIG. 1a, propagates from one of the probes in horizontal direction to the weld (this is a so-called creeping wave), can be used to check a portion of the weld which is situated near the outer surface of the first or second pipeline. Then, not only an interface but also the interior of the weld is checked. The interior situated to the left of the line 80 is then preferably checked by means of creeping waves coming from one of the probes 20.j, while the interior of the weld to the right of the line 80 is preferably checked with creeping waves coming from one of the probes 18.i. Reflection and diffraction of the creeping waves can be waves received with the same probes as or different probes than those with which the creeping waves were transmitted.

Such variants are understood to fall within the scope of the invention.

The invention claimed is:
1. A method for checking a weld between a first metal pipeline and a second metal pipeline, in particular an austenitic weld, characterized in that the method comprises at least the following method steps:
   a. a first ultrasonic beam is transmitted to an interface between the weld and the first pipeline situated on a first side of the weld;
   b. a reflection of the first ultrasonic beam on the interface situated on the first side of the weld is received and a first received signal corresponding thereto is generated;
   c. a second ultrasonic beam different from the first ultrasonic beam is transmitted to the interface situated on the first side of the weld;
   d. a reflection of the second ultrasonic beam on the interface situated on the first side of the weld is received and a second received signal corresponding thereto is generated;
   e. the first received signal and the second received signal are processed in combination for checking the weld;
   wherein
   in step a. the first ultrasonic beam is directed such that the direction in which the first ultrasonic beam is incident on the interface between the weld and the first pipeline deviates from the normal to a surface of the interface between the weld and the first pipeline at the point where the first ultrasonic beam is incident on the interface;

in step b. the reflection of the first ultrasonic beam is measured that comes from a direction that deviates from the direction in which the first ultrasonic beam would reflect on the interface according to the rule that the angle of incidence is equal to the angle of reflection, so that the first ultrasonic received signal represents a diffraction, if any, of the first ultrasonic beam on the interface between the weld and the first pipeline;

in step c. the second ultrasonic beam is directed such that the direction in which the second ultrasonic beam is incident on the interface between the weld and the first pipeline at least substantially does not deviate from the normal to a surface of the interface between the weld and the first pipeline at the point where the second ultrasonic beam is incident on the interface;

in step d. a reflection of the second ultrasonic beam is measured coming from a direction which, at least substantially, coincides with the direction in which the second ultrasonic beam would reflect on a surface of the interface at the point where the second beam is incident on the interface; and wherein the first ultrasonic beam and the second ultrasonic beam are directed to a same area of the interface between the first pipeline and the weld.

2. The method according to claim 1, characterized in that the first and the second ultrasonic beam at the interface between the weld and the first pipeline have a mutually different angle of incidence on the interface.

3. The method according to claim 1, characterized in that in step a. the first ultrasonic beam is supplied to the interface between the weld and the first pipeline via the first pipeline.

4. The method according to claim 3, characterized in that in step a. the first ultrasonic beam is supplied to the first pipeline and propagates via the first pipeline to the weld.

5. The method according to claim 1, characterized in that in step a. the first ultrasonic beam is supplied to the first pipeline from an outer side of the first pipeline.

6. The method according to claim 1, characterized in that in step a. the first ultrasonic beam is supplied from an inner side of the first or second pipeline.

7. The method according to claim 1, characterized in that in step a., for the first ultrasonic beam a longitudinal wave is used.

8. The method according to claim 1, characterized in that in step a. the first ultrasonic beam is focused.

9. The method according to claim 1, characterized in that in step a. the transmitted first ultrasonic beam is a pulsed wave.

10. The method according to claim 1, characterized in that in step b. the reflection of the first ultrasonic beam is measured that comes from a direction which, at least substantially, coincides with the direction in which the first ultrasonic beam is incident on the interface between the first pipeline and the weld.

11. The method according to claim 10, characterized in that the first ultrasonic beam is transmitted and received with one and the same probe.

12. The method according to claim 1, characterized in that the reflection of the first ultrasonic beam is received on an outer side of the first pipeline.

13. The method according to claim 1, characterized in that in step c. the second ultrasonic beam is supplied to the interface between the weld and the first pipeline via the second pipeline and the weld.

14. The method according to claim 1, characterized in that in step c. the second ultrasonic beam, after being transmitted, first of all propagates through the second pipeline to an interface between the second pipeline and a second side of the weld situated opposite the first side of the weld, after which the second ultrasonic beam proceeds to propagate through the weld to the interface between the weld and the first pipeline.

15. The method according to claim 1, characterized in that in step c. the second ultrasonic beam is supplied to the second pipeline from an outer side of the second pipeline.

16. The method according to claim 1, characterized in that in step c. the second ultrasonic beam is supplied to the weld from an inner side of the first or second pipeline.

17. The method according to claim 1, characterized in that in step c., for the second ultrasonic beam a longitudinal wave is used.

18. The method according to claim 1, characterized in that in step c. the second ultrasonic beam is focused.

19. The method according to claim 1, characterized in that the second ultrasonic beam is a pulsed wave.

20. The method according to claim 1, characterized in that the reflection of the second ultrasonic beam is received on an outer side of the second pipeline.

21. The method according to claim 1, characterized in that the second ultrasonic beam is transmitted and received with one and the same probe.

22. The method according to claim 1, characterized in that in step e., on the basis of the first and second received signals, it is determined whether the weld comprises a defect.

23. The method according to claim 22, characterized in that that in step e. it is determined on the basis of the first received signal whether the weld may comprise a defect and it is determined on the basis of the second received signal whether the weld may comprise a defect, it being concluded that the weld actually comprises a defect when both on the basis of the first received signal and on the basis of the second received signal it is concluded that the weld may comprise a defect.

24. The method according to claim 23, characterized in that in step e. the amplitude of the first received signal is compared with a first reference to determine whether the weld may comprise a defect and the amplitude of the second received signal is compared with a second reference to determine whether the weld may comprise a defect.

25. The method according to claim 1, characterized in that the method furthermore comprises at least the following method steps:

f. a third ultrasonic beam is transmitted to the interface between the weld and the first pipeline situated on the first side of the weld;

g. a reflection of the third ultrasonic beam on the interface situated on the first side of the weld, according to the rule that the angle of incidence is equal to the angle of reflection on the surface of the interface between the weld and the first pipeline is received and a third received signal corresponding thereto is generated; and h. the third received signal is analyzed for checking the weld.

26. The method according to claim 25, characterized in that the third beam is directed such that the direction in which the third beam is incident on the interface between the weld and the first pipeline generally deviates from the normal to a surface of the interface between the weld and the first pipeline at the point where the third beam is incident on the interface between the weld and the first pipeline.

27. The method according to claim 25, characterized in that in step f. the third ultrasonic beam is supplied to the interface between the weld and the first pipeline via the first pipeline.

28. The method according to claim 25, characterized in that in step f. the third ultrasonic beam is supplied to the first pipeline and propagates via the first pipeline to the weld.

29. The method according to claim 25, characterized in that in step f. the third ultrasonic beam is supplied to the first pipeline from an outer side of the first pipeline.

30. The method according to claim 25, characterized in that in step f. the third ultrasonic beam is supplied from an inner side of the first or second pipeline.

31. The method according to claim 25, characterized in that in step f., for the third ultrasonic beam a transverse wave is used.

32. The method according to claim 25, characterized in that in step f. the third ultrasonic beam is focused.

33. The method according to claim 25, characterized in that in step f. the transmitted third ultrasonic beam is a pulsed wave.

34. The method according to claim 25, characterized in that in step g. the reflection of the third ultrasonic beam is measured that comes from a direction which, at least substantially, coincides with the direction in which the third ultrasonic beam would reflect on the interface according to the rule that the angle of incidence is equal to the angle of reflection, so that the third ultrasonic received signal represents a reflection, if any, of the third ultrasonic beam on a possible flaw at the interface between the weld and the first pipeline.

35. The method according to claim 34, characterized in that the third ultrasonic beam, after being reflected on the interface between the weld and the first pipeline, propagates to an inner wall of the first pipeline and reflects on the inner wall of the first pipeline to be subsequently received.

36. The method according to claim 25, characterized in that the third ultrasonic beam is generally received with a different probe than the one it is transmitted with.

37. The method according to claim 25, characterized in that in step g. on the basis of an amplitude of the third received signal, the magnitude of a defect, if any, is determined.

38. The method according to claim 37, characterized in that the magnitude of the defect, if any, is determined by comparing the amplitude with a reference.

39. The method according to claim 25, characterized in that on the basis of the third received signal the magnitude of the defect is determined if on the basis of the performance of the method step e. it appears that the weld comprises a defect.

40. The method according to claim 1, characterized in that in a step i. a reflection of the second ultrasonic beam on the interface situated on the first side of the weld is received according to the rule that the angle of incidence is equal to the angle of reflection on the surface of the interface between the weld and the first pipeline is received and a fifth received signal corresponding thereto is generated.

41. The method according to claim 40, characterized in that in a step j. on the basis of an amplitude of the fifth received signal obtained in step h., the magnitude of a defect, if any, is determined.

42. The method according to claim 1, characterized in that in step b. also a reflection of the first ultrasonic beam on an interface of the weld between the weld and the second pipeline is measured to obtain the first received signal and that a fourth ultrasonic beam is supplied to the interface of the weld between the weld and the second pipeline to obtain a fourth received signal, while the first and the fourth ultrasonic beams at the interface between the weld and the second pipeline have a mutually different angle of incidence on the interface between the weld and the second pipeline, and the first received signal and the fourth received signal are processed in combination for checking the interface between the weld and the second pipeline, in particular to determine whether the interface between the weld and the second pipeline comprises a defect.

43. The method according to claim 1, characterized in that an interface between the weld and the second pipeline is checked as the interface between the first pipeline and the weld is checked, while the first ultrasonic beam is also used for checking the interface between the second pipeline and the weld in a same way as the second ultrasonic beam is used for checking the interface between the weld and the first pipeline.

44. The method according to claim 1, characterized in that an interface between the weld and the second pipeline is checked as the interface between the first pipeline and the weld is checked, while the second ultrasonic beam is also used for checking the interface between the second pipeline and the weld in a same way as the first ultrasonic beam is used for checking the interface between the weld and the first pipeline.

45. The method according to claim 1, characterized in that the first ultrasonic beam and the second ultrasonic beam are incident at least substantially on a same area of the interface between the first pipeline and the weld in order for this area of the interface to be checked.

46. The method according to claim 25, characterized in that the third ultrasonic beam is incident at least substantially on the same said area.

47. The method according to claim 25, characterized in that the third ultrasonic beam is directed to said area of the interface between the first pipeline and the weld.

* * * * *

UNITED STATES PATENT AND TRADEMARK OFFICE
CERTIFICATE OF CORRECTION

| | | |
|---|---|---|
| PATENT NO. | : 7,762,137 B2 | Page 1 of 1 |
| APPLICATION NO. | : 10/578492 | |
| DATED | : July 27, 2010 | |
| INVENTOR(S) | : Jan van der Ent, Jacobus Johannes M. van Nisselroij and Edwin Theodorus van Kessel | |

It is certified that error appears in the above-identified patent and that said Letters Patent is hereby corrected as shown below:

Title page, item (75), change "Jacobus Johannes M. van Nisselrolj" to
-- Jacobus Johannes M. van Nisselroij --.

Signed and Sealed this

Twenty-sixth Day of October, 2010

David J. Kappos
*Director of the United States Patent and Trademark Office*